United States Patent [19]

Day

[11] 4,231,120
[45] Nov. 4, 1980

[54] ENDOPROSTHETIC ORTHOPAEDIC DEVICES

[75] Inventor: William H. Day, London, England

[73] Assignee: National Research Development Corporation, London, England

[21] Appl. No.: 943,648

[22] Filed: Sep. 18, 1978

[30] Foreign Application Priority Data

Sep. 22, 1977 [GB] United Kingdom ............... 39553/77

[51] Int. Cl.³ .............................................. A61F 1/24
[52] U.S. Cl. ....................................... 3/1.91; 3/1.911;
3/1.912; 433/173; 128/92 C
[58] Field of Search .................................. 3/1.9–1.913,
3/1; 128/92 C, 92 CA, 92 BC; 32/10 A;
433/173, 176

[56] References Cited

U.S. PATENT DOCUMENTS

| 2,719,522 | 10/1955 | Hudack | 3/1.913 X |
| 3,681,786 | 8/1972 | Lynch | 3/1.91 |
| 3,866,321 | 2/1975 | Valen | 32/10 A |

FOREIGN PATENT DOCUMENTS

| 471394 | 5/1952 | Italy | 3/1.913 |
| 560042 | 3/1975 | Switzerland | 3/1.913 |

*Primary Examiner*—Ronald L. Frinks
*Attorney, Agent, or Firm*—Cushman, Darby & Cushman

[57] ABSTRACT

The securement of an endoprosthetic orthopaedic member of plastics material in cancellous bone involves the provision of a relieved configuration on the member, the upstanding elements of such configuration flexing to afford an interference fit upon translation of the member into a substantially complementary, but slightly undersized recess in the bone. The member is suitably of stem or other elongated form with an annular or helical finned configuration as the upstanding elements. Preferably each such fin configuration includes a sequence of longitudinally separated fins individually extending over a minor circumferential portion of the member. The member will commonly be formed as a one-piece projection from a prosthetic bone joint component.

7 Claims, 1 Drawing Figure

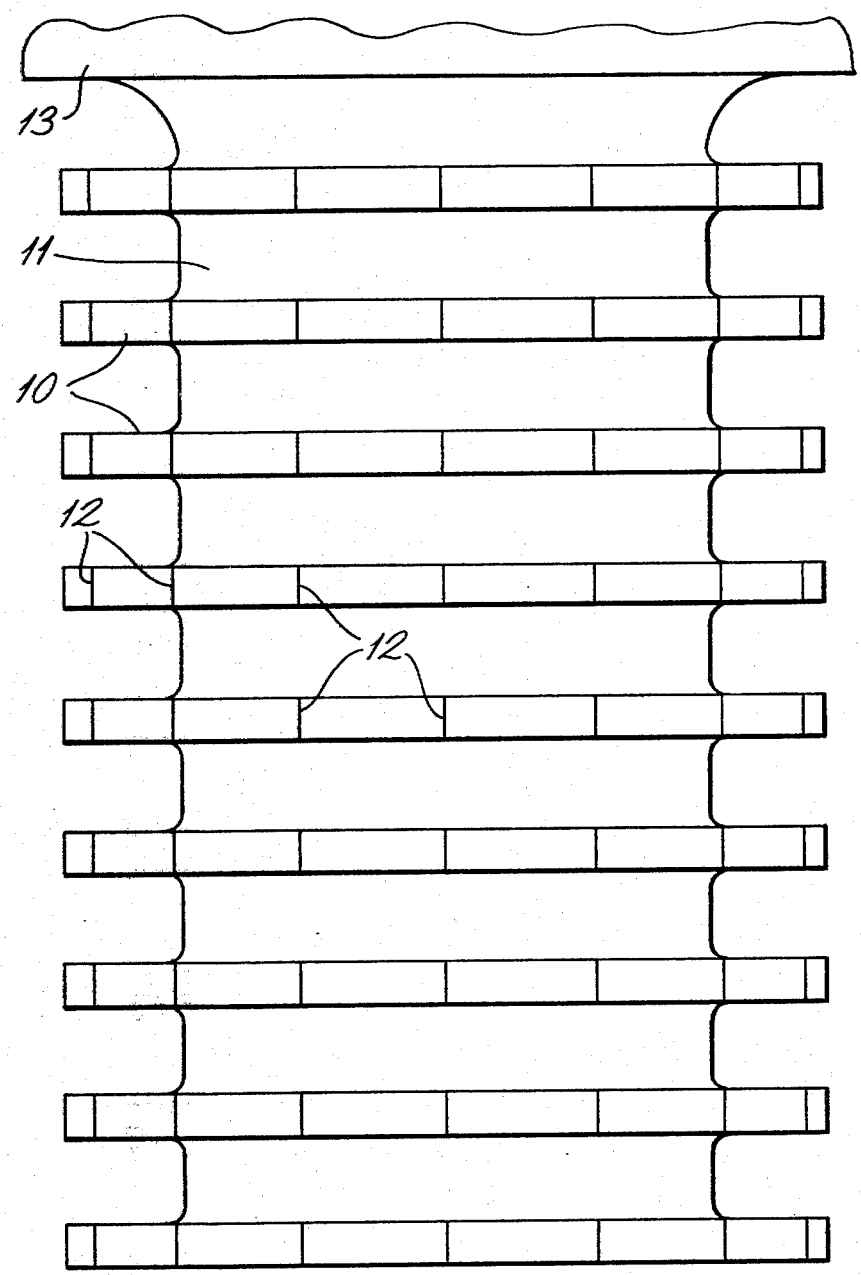

ENDOPROSTHETIC ORTHOPAEDIC DEVICES

This invention concerns endoprosthetic orthopaedic devices and relates more particularly to the securement of such devices in bone.

The techniques for such securement in current usage often employ elongate members to penetrate into cancellous bone. These members are normally located as a clearance fit and secured by the use of a gap-filling medium such as acrylic cement. There are growing tendencies to seek improvement in securement with the use of cement by way of improved site preparation and cement application techniques. At the same time, there is a desire to avoid the use of cement, at least in association with elongate members which penetrate bone, and instead to induce natural securement by bone growth into engagement with such members. The use of screw form members to render cement unnecessary is, of course, limited by the necessity for rotation whereby such members can only be applied individually, and also by the practical requirement for such members to be made of metal.

The present invention seeks to afford some improvement within this situation by the provision of an endoprosthetic orthopaedic member of thermoplastic material having a relieved structure over its surface, each upstanding element of said structure being of such cross-sectional dimensions as to allow securement of said member in an interference fit in cancellous bone by translation alone into a pre-prepared substantially complementary recess in the bone, such fit resulting from flexure of said structure.

Normally, the member wil have an elongated form with said elements projecting transversely from the longitudinal surface of such form.

Preferably the relieved structure is of finned form with each fin extending transversely around the member. Such a structure can comprise fins of annular or helical form which wholly circumscribe the member, but in either case it is preferred that a plurality of fins be provided of which each extends around only a minor circumferential portion of the member. Such a plurality of shorter fins is conveniently provided by cutting or otherwise separating a wholly circumscribing fin at intervals along its length and is advantageous in that the longitudinal ends of the fins engage the bone to resist movement relative thereto under the action of torsional stresses.

It will be appreciated that the cross-sectional dimensions of each fin will be determined in relation to the mechanical properties of the plastics material and cancellous bone. The fins must not be so thick as to be insufficiently flexible and thereby strip the bone into which the member is engaged. At the same time the fins must not be so thin as to be too flexible to produce a sufficient retention force, or alternatively so thin as to break off the fins upon engagement in the bone. Similar considerations apply to the question of fin height, although this appears less critical, and the choice of fin spacing or pitch is also relevant.

It is appropriate to note in this last context that the development of the invention to date has involved members of ultra high molecular weight polyethylene and has led the use of fins of 0.6 to 2 mm thickness and 1 to 6 mm depth, with inter-fin spacing of 1 to 7 mm along the member. Initial development involved substantially cylindrical stem-like members of about 10 mm diameter having projecting fins of up to 1 mm thickness, 3 mm length, and 3 mm spacing, with such fins preferably being about 0.7 mm thick, 2 mm deep, and spaced by 1.5 mm. However further development has involved generally proportionate increases in these values in connection with other members having higher orders of cross-sectional dimensions.

Also, it is to be noted that the invention has been developed primarily for application to endoprosthetic bone joint devices and it is preferred that such a device be made in one piece with one or more finned elongate members projecting therefrom. Alternatively, or in addition, the device itself can be finned in accordance with the present proposal. When there is more than one such member they will have mutually parallel longitudinal axes and such members are, in any case, preferably cylindrical. This application of the invention has the merit that it does not involve the provision of a plurality of parts or materials to a given device as would be the case, for example, with a plastics device to be secured with screws. Also, this applicaton avoids the need for cement around the finned member and allows bone growth into the interstices of the finned structure. It is to be understood however that the relevant device may be partially secured by the use of cement in relation to other portions thereof which are located in the bone less deeply than the finned member or members.

The accompanying drawing illustrates, by way of example, one finned member of a device according to the invention.

The illustrated member is made of the above-mentioned polyethylene and is of basically circular cylindrical form having a longitudinally spaced sequence of annular grooves cut therein to provide a sequence of fins 10. The resultant cylindrical core 11 has a diameter of 8.85 to 9.00 mm, and the fins an outside diameter of 13.00 to 13.15 mm. The fins have a thickness of 0.64 to 0.7 mm, a successive spacing of 1.4 to 1.6 mm, and they are laterally radiused at their roots into the core at 0.2 to 0.3 mm. The annular fins are each cut at 12 in sixteen equally spaced, longitudinal radial planes down to the core of the member.

The illustrated member is shown projecting from part of a body 13 with which it is made in one part together with at least one more member, and this body serves to define an articular surface for a bone joint prosthesis.

While the illustrated member has a plurality of successively spaced annular finned structures, this is not essential and a single finned structure of helical form may be employed. A helical finned structure may better suit manufacture by cutting, although manufacture by moulding may be a preferred alternative which would also allow the use of elongate discrete projections in place of fins.

During initial development of the invention two members such as illustrated have been formed in one piece with the tibial component of an "ICLH" knee joint prosthesis, the two members projecting in parallel manner below the component to effect intracondylar securement.

More recent development has employed a single such member projecting from the base of an acetabular component or so-called cup of a hip joint endoprosthesis, the main body of the cup additionally having fins projecting from its external surface in parallel manner to those of the member but with the higher dimensions of the ranges mentioned above.

Clearly, another possibility is the application of finning to the stem of an endoprosthetic bone joint device which conventionally has a stem for securement by use of bone cement.

I claim:

1. An endoprosthetic orthopaedic component of non-rigid synthetic thermoplastic material, comprising:
a body;
at least one elongate member projecting from said body and formed in one piece therewith;
said member having a generally cylindrical solid core portion with a relieved structure over a major proportion of its longitudinal extent;
said structure being defined by a plurality of like fins circumscribing said core portion;
said fins being successively spaced from one another by a distance longitudinally of said core portion which is greater than the individual thicknesses of the respective fins in the same direction;
each said fin being subdivided into a plurality of angularly discrete portions; and
each said fin having a radial height from said core portion greater than said thickness.

2. An endoprosthetic orthopaedic component of ultra-high molecular weight polyethylene comprising:
a body;
at least one elongate member projecting from said body and formed in one piece therewith;
said member having a generally cylindrical solid core portion with a relieved structure over a major proportion of its longitudinal extent;
said structure being defined by a plurality of like fins circumscribing said core portion;
each said fin being subdivided into a plurality of angularly discrete portions;
each said fin being 0.6 to 2 mm longitudinally thick and 1 to 6 mm radially deep;
and said fins being successively spaced by a 1 to 7 mm distance longitudinally of said core portion.

3. A component according to claim 2, wherein;
each said fin is 0.6 to 1 mm longitudinally thick and 1 to 3 mm radially deep, and said fin spacing distance is 1 to 3 mm.

4. A component according to claim 2, wherein;
each said fin is about 0.7 mm longitudinally thick and 2 mm radially deep, and said fin spacing distance is about 2 mm.

5. A component according to claim 2, wherein:
said core portion is substantially circular cylindrical with a diameter of about 10 mm.

6. For use with a cancellous bone in living tissue, which bone has an artificially-formed recess that is subject to reduction in size due to bone growth,
an endoprosthetic orthopaedic component of non-rigid synthetic thermoplastic material, comprising:
a body;
at least one elongate member projecting from said body and formed in one piece therewith;
said member having a generally cylindrical solid core portion with a relieved structure over a major proportion of its longitudinal extent;
said structure being defined by a plurality of like fins circumscribing said core portion;
said fins being successively spaced from one another by a distance longitudinally of said core portion which is greater than the individual thicknesses of the respective fins in the same direction;
each said fin being subdivided into a plurality of angularly discrete portions; and
each said fin having a radial height from said core portion greater than said thickness;
said fins being slightly transversally oversize relative to the corresponding dimension of said recess, so that engagingly fitting said member in said recess by longitudinal translation alone to produce an interference fit will require some flexure of said fins without fracture thereof, but the amount of said oversize being insufficient to cause stripping of said recess by said fins during said fitting.

7. A method of securing an endoprosthetic component to a bone which comprises:
making said component in one piece from a non-rigid synthetic thermoplastic material with an elongate member projecting therefrom;
forming over a major proportion of the longitudinal extent of said member a relieved structure defined by a plurality of upstanding elements having greater dimensions radially of, than longitudinally of said member;
forming a recess into the cancellous region of said bone, said recess being substantially complementary to, but slightly undersized, relative to said member;
and engaging said member by longitudinal translation alone into said recess to produce an interference fit;
the dimensions of said elements being chosen in dependence upon the mechanical properties of said material and cancellous bone to effect said interference fit by flexure of said elements without fracture thereof and without stripping the wall of said recess.

* * * * *